US012673912B2

(12) United States Patent
Wiederhold et al.

(10) Patent No.: US 12,673,912 B2
(45) Date of Patent: Jul. 7, 2026

(54) METHOD FOR THE PREPARATION OF 1,2-PROPANEDIOL, DIPROPYLENE GLYCOL AND TRIPROPYLENE GLYCOL

(71) Applicant: Evonik Operations GmbH, Essen (DE)

(72) Inventors: Holger Wiederhold, Darmstadt (DE); David Bolz, Frankfurt (DE); Jürgen Glenneberg, Offenbach (DE)

(73) Assignee: Evonik Operations GmbH, Essen (DE)

( * ) Notice: Subject to any disclaimer, the term of this patent is extended or adjusted under 35 U.S.C. 154(b) by 609 days.

(21) Appl. No.: 18/249,980

(22) PCT Filed: Oct. 7, 2021

(86) PCT No.: PCT/EP2021/077764
§ 371 (c)(1),
(2) Date: Apr. 21, 2023

(87) PCT Pub. No.: WO2022/084062
PCT Pub. Date: Apr. 28, 2022

(65) Prior Publication Data
US 2023/0382839 A1     Nov. 30, 2023

(30) Foreign Application Priority Data
Oct. 21, 2020     (EP) .................................... 20203049

(51) Int. Cl.
| | |
|---|---|
| *C07C 41/42* | (2006.01) |
| *C07C 29/48* | (2006.01) |
| *C07C 29/84* | (2006.01) |
| *C07C 41/06* | (2006.01) |

(52) U.S. Cl.
CPC .............. *C07C 41/42* (2013.01); *C07C 29/48* (2013.01); *C07C 29/84* (2013.01); *C07C 41/06* (2013.01)

(58) Field of Classification Search
CPC ....... C07C 29/48; C07C 31/205; C07C 41/05; C07C 43/11; C07C 29/88; C07C 41/44; C07C 29/80; C07C 41/42
USPC ....................................................... 568/695
See application file for complete search history.

(56) References Cited

U.S. PATENT DOCUMENTS

| | | | |
|---|---|---|---|
| 4,308,409 A | 12/1981 | Wu et al. | |
| 10,214,471 B2 | 2/2019 | Wiederhold et al. | |

| | | | |
|---|---|---|---|
| 12,479,783 B2 | 11/2025 | Wiederhold et al. | |
| 12,486,210 B2 | 12/2025 | Wiederhold et al. | |
| 2004/0094478 A1 | 5/2004 | Nobel | |
| 2018/0354878 A1 | 12/2018 | Wiederhold et al. | |
| 2020/0095183 A1 | 3/2020 | Periana et al. | |
| 2023/0382834 A1 | 11/2023 | Wiederhold et al. | |
| 2023/0391699 A1 | 12/2023 | Wiederhold et al. | |
| 2023/0399279 A1 | 12/2023 | Wiederhold et al. | |

FOREIGN PATENT DOCUMENTS

| | | |
|---|---|---|
| CN | 1717399 A | 1/2006 |
| CN | 108623457 A | 10/2018 |
| CN | 108779053 A | 11/2018 |
| WO | 2004/048354 A1 | 6/2004 |
| WO | 2017/089075 | 6/2017 |

OTHER PUBLICATIONS

T. J. Lewis, "The Corrosion of Aluminium in Concentrated Hydrogen Peroxide", J. appl. Chem., vol. 11, Nov. 1961, pp. 405-413.
Indian Office Action dated Sep. 5, 2023, in Indian Application No. 202347034851, with English translation, 6 pages.
Office Action received for U.S. Appl. No. 18/249,825, mailed on Oct. 29, 2025, 42 pages.
International Search Report dated Dec. 20, 2021, in PCT/EP2021/077764, 6 pages.
Sullivan et al., "Propanediois", Ullmann's Encyclopedia of Industrial Chemistry, Jan. 31, 2018, pp. 1-15.
Written Opinion dated Dec. 20, 2021, in PCT/EP2021/077764, 10 pages.
U.S. Appl. No. 18/249,984, filed Apr. 21, 2023, Wiederhold et al.
U.S. Appl. No. 18/249,724, filed Apr. 19, 2023, Wiederhold et al.

(Continued)

*Primary Examiner* — Ana Z Muresan
(74) *Attorney, Agent, or Firm* — Grüneberg Global IP, PLLC

(57)     ABSTRACT

A method can be used for preparing 1,2-propanediol, dipropylene glycol, and tripropylene glycol. The method involves reacting propene with hydrogen peroxide containing nitrate, in the presence of a catalyst mixture containing a phase transfer catalyst and a heteropolytungstate, in a liquid reaction mixture containing an aqueous phase with a maximum apparent pH of 6 and an organic phase. The method then involves separating the reaction mixture into an aqueous phase containing 1,2-propanediol, dipropylene glycol, tripropylene glycol, and nitrate and an organic phase. The method further involves recycling at least part of the separated organic phase to the reaction; hydrogenating the separated aqueous phase using a heterogeneous hydrogenation catalyst to provide a hydrogenated aqueous phase with a reduced nitrate content; and recovering 1,2-propanediol, dipropylene glycol, and tripropylene glycol from the hydrogenated aqueous phase by a sequential multiple-step distillation.

14 Claims, No Drawings

(56)     References Cited

OTHER PUBLICATIONS

U.S. Appl. No. 18/249,584, filed Apr. 19, 2023, Wiederhold et al.
U.S. Appl. No. 18/249,695, filed Apr. 19, 2023, Wiederhold et al.
U.S. Appl. No. 18/249,729, filed Apr. 19, 2023, Bolz et al.
U.S. Appl. No. 18/249,908, filed Apr. 20, 2023, Wiederhold et al.
U.S. Appl. No. 18/249,982, filed Apr. 21, 2023, Wiederhold et al.
U.S. Appl. No. 18/249,660, filed Apr. 19, 2023, Wiederhold et al.
U.S. Appl. No. 18/249,906, filed Apr. 20, 2023, Wiederhold et al.
U.S. Appl. No. 18/249,825, filed Apr. 20, 2023, Wiederhold et al.

METHOD FOR THE PREPARATION OF 1,2-PROPANEDIOL, DIPROPYLENE GLYCOL AND TRIPROPYLENE GLYCOL

CROSS-REFERENCE TO RELATED APPLICATIONS

This application is the National Stage entry under § 371 of International Application No. PCT/EP2021/077764, filed on Oct. 7, 2021, and which claims the benefit of priority to European Application No. 20203049.0, filed on Oct. 21, 2020. The content of each of these applications is hereby incorporated by reference in its entirety.

BACKGROUND OF THE INVENTION

Field of the Invention

The present invention relates to a method for the preparation of 1,2-propanediol, dipropylene glycol and tripropylene glycol by reacting propene with hydrogen peroxide which contains nitrate.

Description of Related Art

In a well-established process used in the industry, 1,2-propanediol is prepared by reacting propene oxide with water. Propene oxide can be made on an industrial basis using the HPPO process comprising the reaction of propene with hydrogen peroxide in the presence of a titanium zeolite catalyst and an organic solvent. Propene oxide is isolated and purified prior to a second step of reacting it with water to make 1,2-propanediol. As valuable side product small amounts of dipropylene glycol and tripropylene glycol are obtained.

WO 2017/089075 discloses a method for producing 1,2-propanediol from propene and hydrogen peroxide comprising: a) reacting propene with hydrogen peroxide in the presence of a catalyst mixture comprising a phase transfer catalyst and a heteropolytungstate, wherein the reaction is carried out in a liquid mixture comprising an aqueous phase with a maximum pH of 6 and an organic phase, b) dividing the two-phase mixture from step a) into an aqueous phase and an organic phase containing propylene oxide, c) returning the propylene oxide contained in the separated organic phase into the reaction from step a) and d) separating 1,2-propanediol from the aqueous phase separated in step b).

Both dipropylene glycol and tripropylene glycol are valuable by-products in the manufacture of 1,2-propanediol and it is desirable to recover these by-products in an industrial process for making 1,2-propanediol.

SUMMARY OF THE INVENTION

The inventor of the present invention has now found that the use of an aqueous hydrogen peroxide solution containing nitrate, which is commonly used for preventing corrosion of aluminum storage tanks, in the oxidation process of WO 2017/089075 can lead to hazards in the distillative work-up of the aqueous phase containing the 1,2-propanediol product, because distillative work-up for recovering dipropylene glycol and tripropylene glycol may lead to bottoms products which contain nitrate at a level where it may cause unwanted oxidative side reactions in the column reboiler which produce nitrogen oxides and may even cause a runaway reaction with high boiling organic by-products present in the column bottoms. The inventor of the present invention has also found that these hazards may be prevented by hydrogenating the aqueous phase with a heterogeneous hydrogenation catalyst prior to recovering 1,2-propanediol, dipropylene glycol and tripropylene glycol by distillation.

Subject of the invention is therefore a method for the preparation of 1,2-propanediol, dipropylene glycol and tripropylene glycol comprising:

a) reacting propene with hydrogen peroxide containing nitrate in the presence of a catalyst mixture comprising a phase transfer catalyst and a heteropolytungstate in a liquid reaction mixture comprising an aqueous phase with a maximum apparent pH of 6 and an organic phase;

b) separating the reaction mixture into an aqueous phase ($P_a$) comprising 1,2-propanediol, dipropylene glycol, tripropylene glycol and nitrate and an organic phase ($P_o$);

c) recycling at least a part of the separated organic phase ($P_o$) to the reaction step a);

d) hydrogenating the aqueous phase ($P_a$) separated in step b) using a heterogeneous hydrogenation catalyst to provide a hydrogenated aqueous phase; and e) recovering 1,2-propanediol, dipropylene glycol and tripropylene glycol from the hydrogenated aqueous phase of step d) by a sequential multiple step distillation, comprising a first water distillation step and optionally further water distillation steps, each providing an overhead product comprising water and a bottoms product which is passed to the next distillation step, a subsequent first glycols distillation step providing an overhead product comprising 1,2-propanediol and a bottoms product which is passed to the next distillation step, a subsequent second glycols distillation step providing an overhead product comprising dipropylene glycol and a bottoms product which is passed to the next distillation step, and a subsequent third glycols distillation step providing an overhead product comprising tripropylene glycol and a residuals bottoms product.

Another subject of the invention is the use of a hydrogenation step to reduce the nitrate content of an aqueous mixture subjected to a distillation sequence for separating tripropylene glycol as an overhead product in a method for the preparation of 1,2-propanediol, dipropylene glycol and tripropylene glycol, the method comprising:

a) reacting propene with hydrogen peroxide containing nitrate in the presence of a catalyst mixture comprising a phase transfer catalyst and a heteropolytungstate in a liquid reaction mixture comprising an aqueous phase with a maximum apparent pH of 6 and an organic phase;

b) separating the reaction mixture into an aqueous phase ($P_a$) comprising 1,2-propanediol, dipropylene glycol, tripropylene glycol and nitrate and an organic phase ($P_o$);

c) recycling at least a part of the separated organic phase ($P_o$) to the reaction step a);

d) hydrogenating the aqueous phase ($P_a$) separated in step b) using a heterogeneous hydrogenation catalyst to provide a hydrogenated aqueous phase; and e) recovering 1,2-propanediol, dipropylene glycol and tripropylene glycol from the hydrogenated aqueous phase of step d) by a sequential multiple step distillation, comprising a first water distillation step and optionally further water distillation steps, each providing an overhead product comprising water and a bottoms product which is passed to the next distillation step, a subsequent first glycols distillation step providing an overhead product comprising 1,2-propanediol and a bottoms product which is passed to the next distillation step, a subsequent second glycols distillation step providing an overhead product comprising dipropylene glycol and a bottoms product which is passed to the next distillation step, and a subsequent third glycols distillation step providing an overhead product comprising tripropylene glycol and a residuals bottoms product.

DETAILED DESCRIPTION OF THE INVENTION

In the method of the present invention, propene is reacted in a step a) with hydrogen peroxide in the presence of a catalyst mixture comprising a phase transfer catalyst and a heteropolytungstate. This reaction is carried out in a liquid reaction mixture which comprises an aqueous phase with a maximum apparent pH of 6 and an organic phase.

Propene can be used in pure form or in a mixture with propane, wherein the proportion of propane may be up to 20 mol %. The proportion of propane in the propene used is preferably less than 5 mol %. Propene is preferably employed in a molar excess to hydrogen peroxide, preferably in a molar ratio of propene to hydrogen peroxide of from 1.1:1 to 10:1.

The hydrogen peroxide used in step a) contains nitrate. Hydrogen peroxide is preferably used in the form of an aqueous solution, preferably with a hydrogen peroxide content of 10 to 80% by weight, particularly preferably 30 to 70% by weight. Any commercially available grade of aqueous hydrogen peroxide solutions containing nitrate can be used. A crude hydrogen peroxide product obtained in the extraction stage of the anthraquinone process for producing hydrogen peroxide with added nitrate for preventing aluminum corrosion may also be used. Preferably, an aqueous hydrogen peroxide solution is used which contains from 5 to 500 mg/kg of nitrate, calculated based on the weight of the aqueous hydrogen peroxide solution.

The catalyst mixture used in step a) comprises a heteropolytungstate. The heteroatom is preferably phosphorus or arsenic and is particularly preferably phosphorus, i.e. the heteropolytungstate is particularly preferably a polytungstophosphate. Heteropolytungstates are well known to a person skilled in the art. Preferred polytungstophosphates have a molar ratio of phosphorus to tungsten in the range of from 1:2 to 1:12. The polytungstophosphate is preferably generated in situ by combining phosphoric acid and sodium tungstate, which can be carried out in the liquid reaction mixture itself or prior to adding the polytungstophosphate to the liquid reaction mixture. Phosphoric acid and sodium tungstate are preferably employed at a molar ratio of phosphorus to tungsten in the range of from 1:2 to 10:1, preferably from 4:1 to 8:1. The heteropolytungstate reacts with hydrogen peroxide in the liquid reaction mixture to form peroxotungstates and peroxotungstophosphates, for example $PO_4[WO(O_2)_2]_4^{3-}$ and $HPO_4[WO(O_2)_2]_2^{2-}$ as well as partially protonated forms thereof, which are presumably the catalytically active species for oxidizing propene.

The catalyst mixture used in step a) also comprises a phase transfer catalyst. The phase transfer catalyst comprises a cation or a compound which forms a cation in the aqueous phase, whereby the cation can form a salt with a peroxotungstate or heteropolyperoxotungstate, which salt is soluble in the organic phase of the liquid reaction mixture. The phase transfer catalyst preferably comprises a singly-charged cation or a compound which forms a singly-charged cation in the aqueous phase. Suitable as phase transfer catalyst are tertiary amines, tertiary and quaternary ammonium salts, and quaternary phosphonium salts. Suitable counterions for tertiary and quaternary ammonium salts are the anions chloride, bromide, nitrate, sulphate, hydrogen phosphate, dihydrogen phosphate, methyl sulfonate, methyl sulphate and ethyl sulphate. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, where the molar ratio refers to the cations or compounds forming cations in the employed phase transfer catalyst and to the employed amount of tungsten.

In a preferred embodiment, the phase transfer catalyst is a tertiary amine or a tertiary or a quaternary ammonium salt which comprises in total at least 12 carbon atoms, preferably from 12 to 60 carbon atoms. Preferred are tetraalkylammonium salts. Suitable tertiary amines are for example dodecyldimethylamine, hexadecyldimethylamine, octadecyldimethylamine, tributylamine and trioctylamine. Suitable tertiary ammonium salts are the protonation products of these tertiary amines. Suitable quaternary ammonium salts are for example dodecyltrimethylammonium salts, hexadecyltrimethylammonium salts, octadecyltrimethylammonium salts, methyltributylammonium salts and methyltrioctylammonium salts. More preferably, the phase transfer catalyst comprises a tertiary or quaternary ammonium ion having the structure $R^1R^2R^3NR^{4+}$, wherein $R^1$, $R^2$ and $R^3$ are the same or different and are each selected from alkyl groups having from 8 to 10 carbon atoms and $R^4$ is hydrogen or methyl. Most preferably, the phase transfer catalyst comprises methyltri(octyl/decyl)ammonium methylsulfate (CAS No. 2387913-24-6).

In another preferred embodiment, the phase transfer catalyst comprises at least one salt having a tertiary or quaternary ammonium ion of the structure $R^1R^2R^3R^4N^+$, where $R^1$ is a $Y—O(C=O)R^5$ group with Y being $CH_2CH_2$, $CH(CH_3)CH_2$ or $CH_2CH(CH_3)$ and $R^5$ being an alkyl group or alkenyl group having 11 to 21 carbon atoms, $R^2$ is hydrogen or an alkyl group having 1 to 4 carbon atoms, and $R^3$ and $R^4$ are each independently $R^1$, an alkyl group having 1 to 4 carbon atoms or $Y—OH$.

Preferred are quaternary ammonium salts with methylsulphate as the counterion, where $R^2$ is a methyl group and $R^5$ is a linear alkyl group or alkenyl group. Particularly preferred are the salts $(CH_3)_3N^+CH_2CH_2O(C=O)R^5CH_3OSO_3^-$, $(CH_3)_2N^+(CH_2CH_2OH)(CH_2CH_2O(C=O)R^5)$ $CH_3OSO_3^-$, $(CH_3)_2N^+CH_2CH_2O(C=O)R^5)_2$ $CH_3OSO_3^-$, $CH_3N^+(CH_2CH_2OH)_2(CH_2CH_2O(C=O)R^5)$ $CH_3OSO_3^-$, $CH_3N^+(CH_2CH_2OH)(CH_2CH_2O(C=O)R^5)_2$ $CH_3OSO_3^-$, $CH_3N^+(CH_2CH_2O(C=O)R^5)_3CH_3OSO_3^-$, $(CH_3)_3N^+CH_2CH(CH_3)O(C=O)R^5CH_3OSO_3^-$, $(CH_3)_2N^+$ $(CH_2CH(CH_3)OH)(CH_2CH(CH_3)O(C=O)R^5)$ $CH_3OSO_3^-$ and $(CH_3)_2N^+(CH_2CH(CH_3)O(C=O)R^5)_2CH_3OSO_3^-$, in which $R^5$ is in each case a linear alkyl group or alkenyl group having 11 to 21 carbon atoms. Most preferred is the salt $(CH_3)_2N^+(CH_2CH(CH_3)O(C=O)R^5)_2CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or triisopropanolamine with a fatty acid and subsequent quaternization with dimethyl sulphate. These phase transfer catalysts have the advantage that they are readily biodegradable, unlike tetraalkylammonium salts, and can be introduced into a biological treatment plant without further pretreatment. The salts with methylsulphate as anion are also less corrosive than tetraalkylammonium halides.

The reaction of step a) is carried out in a liquid reaction mixture which comprises two liquid phases, an aqueous phase with a maximum apparent pH of 6 and an organic phase. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the aqueous phase of the reaction mixture, which comprises hydrogen peroxide and glycols, is different than the normal potential in pure water. The apparent pH of the aqueous phase is preferably maintained in the range from 1.0 to 3.5, particularly preferably in the range from 2.0 to 3.0. The apparent pH can be maintained in this range by addition of acid, preferably sulphuric acid or phosphoric acid, or by addition of base, preferably aqueous sodium hydroxide solution. Adjusting the apparent pH in the preferred range provides high selectivity for 1,2-propanediol and prevents enriching propene oxide in the aqueous phase, which simplifies the subsequent separation of propylene glycols from the aqueous phase.

The weight ratio of hydrogen peroxide to water is preferably within the range of from 0.05 to 1.5, more preferably from 0.10 to 0.7 and most preferably from 0.15 to 0.45. The concentration of hydrogen peroxide in the aqueous phase of step a) is preferably kept within a range of from 0.1 to 5% by weight, preferably from 0.12 to 1.0% by weight.

The reaction is preferably conducted at a temperature in the range of from 50 to 110° C., more preferably 60 to 100° C. and particularly preferably 70 to 90° C. The reaction pressure is preferably higher than the vapor pressure of propene at the reaction temperature to ensure that most of the propene is present in the liquid organic phase of the liquid mixture.

The reaction of step a) can be carried out with or without addition of an organic solvent. The reaction is preferably conducted in the presence of at least one organic solvent having a boiling point of more than 100° C., preferably more than 120° C., which has a solubility in water of less than 250 mg/kg at 20° C. Suitable as solvents are alcohols having one or more hydroxyl groups, ethers, esters, ketones and alkylated aromatic hydrocarbons. Adding a solvent can improve extraction of a salt formed of the heteropolytungstate and the phase transfer catalyst into the organic phase. Preferably the amount of organic solvent is selected to provide a proportion of organic solvent in the organic phase during the reaction in the range of from 10 to 90% by weight.

In a preferred embodiment, the organic solvent comprises an epoxidized fatty acid methyl ester. The epoxidized fatty acid methyl ester can be formed in situ in the reaction mixture of step a) by employing a fatty acid methyl ester with unsaturated fatty acid groups which reacts with hydrogen peroxide to the epoxidized fatty acid methyl ester. Particularly preferred are epoxidized fatty acid methyl esters which comprise fatty acid groups originating from vegetable oils, in particular soybean oil. The epoxidized fatty acid methyl esters have the advantage that they have low solubility in the aqueous phase.

In another preferred embodiment, the solvent comprises an alkylated aromatic hydrocarbon having 8 to 12 carbon atoms. Suitable alkylated aromatic hydrocarbons are, for example, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3,5-trimethylbenzene (mesitylene), 1-ethyl-2-methylbenzene, 1-ethyl-3-methylbenzene and 1-ethyl-4-methylbenzene and n-propylbenzene. Preferably, hydrocarbon mixtures comprising more than 50% by weight, particularly preferably more than 80% by weight, of alkylated aromatic hydrocarbons having 8 to 12 carbon atoms are used as solvent. The use of these solvents enables extracting most of the peroxotungstates into the organic phase of the reaction mixture and recycling them, which allows for operating the process without a need for recovering heteropolytungstate from the aqueous phase of the reaction mixture of step a). The phase transfer catalyst, the molar ratio of phase transfer catalyst to heteropolytungstate, the molar ratio of heteroatom of the heteropolytungstate to tungsten, the molar ratio of propene to hydrogen peroxide and the amount of solvent are then preferably selected to transfer as much as possible of the tungsten present in the liquid reaction mixture into the organic phase.

The phase transfer catalyst, the heteropolytungstate and the optionally used solvent can be added in step a) of the method of the present invention separately or in the form of mixtures containing two or all three of these components. Preferably, a solvent is used in step a) and the phase transfer catalyst and the heteropolytungstate are added dissolved in an organic phase comprising the solvent.

The reaction of step a) may be carried out in batch or continuously, with a continuous reaction being preferred. In a continuous reaction, the concentration of hydrogen peroxide in the aqueous phase is preferably maintained in the range of 0.1 to 5% by weight, particularly preferably 0.5 to 3% by weight. The concentration of hydrogen peroxide can be adjusted in this range by appropriate selection of the reaction temperature, the molar ratio of propene to hydrogen peroxide and the residence time of the liquid mixture in the reactor in which the reaction takes place. The residence time of the reaction mixture is preferably adjusted to maintain a hydrogen peroxide conversion in the range of from 80 to 99%.

During the reaction, the liquid mixture is preferably mixed in order to generate a large phase interface between the aqueous phase and the organic phase. For this purpose, the reaction is preferably carried out continuously in a loop reactor which has fixed internals and the liquid mixture is passed through the loop reactor at a flow rate which generates a turbulent flow at the internals. Baffles, static mixing elements, structured packings or random packings can be used as internals for this purpose. In combination to these internals or as an alternative, heat exchangers, such as plate heat exchangers or tube bundle heat exchangers, may be used, in which turbulent flow is generated, for example between the plates of a plate heat exchanger or in the tubes of a tube bundle heat exchanger.

In step a) of the method of the present invention, the reaction heat generated by the oxidation of propene is preferably removed at least partially. Preferably, all or a part of the generated reaction heat is removed by cooling the reaction mixture in a heat exchanger. More preferably, the reaction is carried out continuously in a loop reactor which comprises a heat exchanger within the reactor loop for cooling the reaction mixture.

In step b) of the method of the present invention, the liquid reaction mixture provided by step a) is separated into an aqueous phase ($P_a$) comprising 1,2-propanediol, dipropylene glycol, tripropylene glycol and nitrate and an organic phase ($P_o$). The separation of the two-phase reaction mixture provided by step a) is preferably carried out in a settler vessel. The two-phase reaction mixture is preferably passed through a coalescer element comprising a structured packing or a random packing with a surface wetted by the dispersed phase of the two-phase mixture in order to achieve a more complete separation.

The aqueous phase ($P_a$) typically comprises water, unreacted hydrogen peroxide and nitrate and the reaction products 1,2-propanediol, dipropylene glycol and tripropylene glycol. The aqueous phase typically also contains reaction byproducts, such as 1-hydroperoxy-2-propanol and 2-hydroperoxy-1-propanol formed by reaction of propene oxide with hydrogen peroxide, and hydroxyacetone formed by further oxidation of 1,2-propanediol. The aqueous phase typically may also comprise phosphoric acid and sodium salts of phosphoric acid if a polytungstophosphate generated in situ by combining phosphoric acid and sodium tungstate is used in step a). The organic phase ($P_o$) comprises unreacted propene and propene oxide that is formed as intermediate when propene is reacted with hydrogen peroxide and has not been hydrolyzed to 1,2-propanediol. The organic phase ($P_o$) typically also comprises one or more salts formed of the heteropolytungstate and the cation of the phase transfer catalyst. The organic phase ($P_o$) will also comprise propane, if the propene starting material contains propane, and organic solvent, if an organic solvent having a low solubility in water is used as described further above.

In step c) of the method of the present invention, at least a part of the separated organic phase ($P_o$) is recycled to the reaction step a). Thereby, propene oxide present in the organic phase ($P_o$) is recycled to step a) in order to achieve a complete conversion of propene to 1,2-propanediol, dipropylene glycol and tripropylene glycol. Preferably, the heteropolytungstate present in the organic phase ($P_o$) is recycled into step a), and it is particularly preferred to recycle substantially all of the catalyst mixture that is present in the organic phase into step a).

The organic phase ($P_o$) separated from the liquid reaction mixture provided by step a) may be recycled to step a) without further treatment. If the propene fed to step a) contains propane, it is preferred to separate a stream of unreacted propene from the organic phase in step c) before the organic phase is recycled to step a), with the separated stream of unreacted propene containing as much propane as the impure propene fed to step a). This way, an accumulation of propane in the organic phase of the reaction mixture of step a) can be avoided for a continuous reaction. The separated stream of unreacted propene may be passed to a C3 splitter for separating propene and propane and the recovered propene may be recycled to step a).

The aqueous phase ($P_a$) obtained in step b) is preferably further processed without recycling any part of it directly or indirectly to step a).

In step d) of the method according to the present invention, the aqueous phase comprising 1,2-propanediol, dipropylene glycol, tripropylene glycol and nitrate obtained in separation step b) is hydrogenated, using a heterogeneous hydrogenation catalyst to provide a hydrogenated aqueous phase. The hydrogenation is preferably carried out using a supported hydrogenation catalyst comprising one or more metals from the group of Ru, Rh, Pd, Pt, Ag, Ir, Fe, Cu, Ni and Co on a support, wherein activated carbon, $SiO_2$, $TiO_2$, $ZrO_2$, $Al_2O_3$ and aluminium silicates are preferred as support materials. Preference is given to hydrogenation catalysts comprising ruthenium as active metal. The catalytic hydrogenation is preferably carried out at a partial hydrogen pressure of 5 to 50 bar, preferably 5 to 35 bar, more preferred 7 to 30 bar, even more preferred 8 to 25 bar, and a temperature of 80° C. to 140° C., preferably 90° C. to 120° C. The hydrogenation catalyst may be used as a suspension or as a fixed bed, a trickle bed hydrogenation with a fixed bed catalyst being preferred. The hydrogenation converts nitrate and nitric acid present in the aqueous phase ($P_a$) to molecular nitrogen and volatile nitrogen oxides. The hydrogenation can also prevent problems caused by decomposition of hydrogen peroxide, which has not reacted in step a), in step e) of recovering 1,2-propanediol, dipropylene glycol and tripropylene glycol. The hydrogenation also converts the by-products 1-hydroperoxy-2-propanol, 2-hydroperoxy-1-propanol and hydroxyacetone formed in step a) to 1,2-propanediol and thereby improves the yield of 1,2-propanediol.

In step e) of the method of the present invention, 1,2-propanediol, dipropylene glycol and tripropylene glycol are recovered from the hydrogenated aqueous phase of step d) by a sequential multiple step distillation. In a first water distillation step, an overhead product comprising water is separated from a bottoms product comprising 1,2-propanediol, dipropylene glycol and tripropylene glycol as well as high-boiling organic compounds. Since nitrate is hydrogenated in step d) to products which are much more volatile than water, the bottoms product of the first water distillation step containing the glycols will have a low nitrate content and may be essentially free of nitrate. The sequential multiple step distillation of step e) may comprise further water distillation steps and preferably comprises several water distillation steps carried out with heat integration in multi-effect evaporators. In a subsequent first glycols distillation step, the final bottoms product of the one or more water distillation steps is separated into an overhead product comprising 1,2-propanediol and a bottoms product comprising dipropylene glycol and tripropylene glycol as well as high-boiling organic compounds. In a second glycols distillation step, the bottoms product of the first glycols distillation step is separated into an overhead product comprising dipropylene glycol and a bottoms product comprising tripropylene glycol as well as high-boiling organic compounds. In a third glycols distillation step, the bottoms product of the second glycols distillation step is separated into an overhead product comprising tripropylene glycol and a bottoms product comprising high-boiling organic compounds. The glycols distillation steps are preferably carried out at reduced pressure, preferably at pressures which decrease along the series of glycols distillation steps. Preferably, a sequence of distillation steps as described in Ullmann's Encyclopedia of Industrial Chemistry, online edition, entry "Propanediols", page 4, DOI 10.1002/14356007.a22_163.pub2 is used where an overhead product comprising water is separated from a bottoms product comprising 1,2-propanediol, dipropylene glycol and tripropylene glycol in a series of two to four distillation steps, followed by successive vacuum distillation steps which provide 1,2-propanediol, dipropylene glycol and tripropylene glycol as overhead products and a bottoms product containing higher boiling organic compounds and salts.

The multiple step distillation, necessary for recovering tripropylene glycol from the aqueous phase ($P_a$) of the propene oxidation reaction of step a), provides a bottoms product in the third glycols distillation step which has a much smaller volume than the aqueous phase ($P_a$). Therefore, non-volatile impurities contained in the aqueous phase ($P_a$) will be strongly enriched in this bottoms phase and even small amounts of nitrate present in the aqueous phase ($P_a$) due to the use of hydrogen peroxide containing nitrate in step a) can be enriched to levels where reaction of nitrate with the higher boiling organic compounds in the column reboiler can reach a hazardous level. Hydrogenating the aqueous phase ($P_a$) in step d) reduces the nitrate content of the aqueous phase ($P_a$) to a low level which prevents hazards by nitrate enrichment in the subsequent distillation steps for recovering 1,2-propanediol, dipropylene glycol and tripropylene glycol.

The present invention will now be explained in more detail with reference to an example.

EXAMPLE 500 g of the aqueous phase separated from a reaction mixture of reacting propene with a commercial hydrogen peroxide solution containing sodium nitrate in the presence of a C10 alkyl benzenes solvent and a catalyst system obtained by combining phosphoric acid, sodium tungstate dihydrate and methyltri(octyl/decyl)ammonium methylsulfate were charged to a 1 l spinning basket autoclave containing 75 g of a 2% by weight ruthenium on activated carbon supported catalyst in the spinning basket. The autoclave was flushed with nitrogen, pressurized with hydrogen to 0.6 MPa and heated to 90° C. The autoclave was then further pressurized with hydrogen to 1.6 MPa, the stirrer was started, and hydrogenation was carried out at 90° C. and 1.6 MPa hydrogen pressure for 3.5 h with the basket spinning. The aqueous phase was analyzed for hydrogen peroxide by redox titration and for organic products by capillary GC (25 m CP-WAX-52 CB column from Agilent, He carrier gas, temperature program starting at 50° C. with ramps of 20 K/min to 90° C., 10 K/min to 220° C. and 5 K/min to 235° C., FID detector) prior to and after the hydrogenation. Table 1 shows the analysis data. Analysis of the hydrogenated aqueous phase for nitrate by ion chromatography with a conductivity detector (Metrohm A Supp 5-250 column (polyvinyl alcohol with quaternary ammonium groups), 0.5 ml/min aqueous eluent with 1 mmol/l NaHCO$_3$ and 3.2 mmol/A Na$_2$CO$_3$, aqueous suppressor regenerant with 100 mmol/l sulfuric acid and 20 mmol/l oxalic acid) showed a broad peak at the retention time for nitrate on an uneven baseline with an area indicating a content of no more than 12 ppm nitrate, whereas analysis of the non-hydrogenated aqueous phase typically showed a nitrate content of about 35 ppm.

TABLE 1

Composition of the aqueous phase prior to and
after hydrogenation (all values in % by weight)

| Component | Prior to hydrogenation | After hydrogenation |
|---|---|---|
| 1,2-propanediol | 19.7 | 20.35 |
| Hydroxyacetone | 0.3 | 0 |
| Acetaldehyde | 0.1 | 0 |
| Acetic acid | 0.1 | 0.1 |
| Hydrogen peroxide | 0.5 | 0.003 |

The invention claimed is:

1. A method for the preparation of 1,2-propanediol, dipropylene glycol, and tripropylene glycol, the method comprising:
   a reacting propene with hydrogen peroxide containing nitrate in the presence of a catalyst mixture, comprising a phase transfer catalyst and a heteropolytungstate, in a liquid reaction mixture comprising an aqueous phase with a maximum apparent pH of 6 and an organic phase, wherein apparent pH is a value determined by measurement with a glass electrode employing a commercial pH meter calibrated with aqueous buffer solutions of known pH for measuring dilute aqueous solutions forming a liquid reaction mixture comprising an aqueous phase comprising 1,2-propanediol, dipropylene glycol, tripropylene glycol, and nitrate and an organic phase;
   b) separating the liquid reaction mixture into a separated aqueous phase ($P_a$) comprising 1,2 propanediol, dipropylene glycol, tripropylene glycol, and nitrate, and a separated organic phase ($P_o$);
   c) recycling at least a part of the separated organic phase ($P_o$) to a);
   d) hydrogenating the separated aqueous phase ($P_a$) with a heterogeneous hydrogenation catalyst thereby converting nitrate and nitric acid present in said aqueous phase ($P_a$) to molecular nitrogen and volatile nitrogen oxides, to provide a hydrogenated aqueous phase; and
   e) recovering the 1,2-propanediol, the dipropylene glycol, and the tripropylene glycol from the hydrogenated aqueous phase by a sequential multiple step distillation, comprising
      a first water distillation step and optionally further water distillation steps, each providing an overhead product comprising water and a bottoms product which is passed to a subsequent first glycols distillation step,
      the subsequent first glycols distillation step, providing a first overhead product comprising the 1,2 propanediol and a first bottoms product which is passed to a subsequent second glycols distillation step,
      the subsequent second glycols distillation step, providing a second overhead product comprising the dipropylene glycol and a second bottoms product which is passed to a subsequent third glycols distillation step, and
      the subsequent third glycols distillation step, providing a third overhead product comprising the tripropylene glycol and a residuals bottoms product.

2. The method of claim 1, wherein the heterogeneous hydrogenation catalyst comprises ruthenium.

3. The method of claim 1, wherein the hydrogenation is conducted at a temperature in a range of from 50 to 200° C.

4. The method of claim 1, wherein the separated aqueous phase ($P_a$) is further processed without recycling any part of it directly or indirectly to a).

5. The method of claim 1, wherein a) is carried out continuously, and
   wherein a concentration of hydrogen peroxide in the aqueous phase of a) is from 0.1 to 5% by weight.

6. The method of claim 1, wherein a) is carried out continuously in a loop reactor comprising internals in a tubular section, and wherein the liquid reaction mixture is passed through the loop reactor at a flow rate sufficient to provide turbulent flow at said internals.

7. The method of claim 1, wherein a) is conducted in the presence of phosphoric acid.

8. The method of claim 1, wherein the heteropolytungstate is a polytungstophosphate.

9. The method of claim 1, wherein the organic phase in a) comprises an organic solvent having a boiling point of more than 100° C. at atmospheric pressure and a solubility in water at 20° C. of less than 250 mg/kg.

10. The method of claim 1, wherein the phase transfer catalyst comprises at least one selected from the group consisting of a tertiary amine, a tertiary ammonium salt, and a quaternary ammonium salt; and wherein the tertiary amine, the tertiary ammonium salt, and the quaternary ammonium salt comprises in total at least 12 carbon atoms.

11. The method of claim 10, wherein the phase transfer catalyst comprises a tertiary or quaternary ammonium ion having the structure $R^1R^2R^3NR^{4+}$, wherein $R^1$, $R^2$, and $R^3$ are the same or different and are each an alkyl group having from 8 to 10 carbon atoms, and $R^4$ is hydrogen or methyl.

12. The method of claim 1, wherein the hydrogenated aqueous phase has a reduced nitrate content compared to the separated aqueous phase ($P_a$).

13. The method of claim 3, wherein the hydrogenation is conducted at a temperature in a range of from 80 to 140° C.

14. The method of claim 9, wherein the organic solvent is an alkylated aromatic hydrocarbon having 8 to 12 carbon atoms.

\* \* \* \* \*